United States Patent
Venkatesan et al.

(10) Patent No.: US 11,280,868 B2
(45) Date of Patent: Mar. 22, 2022

(54) IMAGE ENHANCEMENT WITH VARIABLE NUMBER OF EXCITATION (NEX) ACQUISITIONS ACCELERATED USING COMPRESSED SENSING

(71) Applicant: GE Precision Healthcare LLC, Wauwatosa, WI (US)

(72) Inventors: Ramesh Venkatesan, Karnataka (IN); Imam Ahmed Shaik, Karnataka (IN); Rajagopalan Sundaresan, Karnataka (IN); Ashok Kumar P Reddy, Karnataka (IN)

(73) Assignee: GE Precision Healthcare LLC, Wauwatosa, WI (US)

( * ) Notice: Subject to any disclaimer, the term of this patent is extended or adjusted under 35 U.S.C. 154(b) by 58 days.

(21) Appl. No.: 16/904,801

(22) Filed: Jun. 18, 2020

(65) Prior Publication Data
US 2020/0400767 A1    Dec. 24, 2020

(30) Foreign Application Priority Data
Jun. 19, 2019    (IN) .............................. 201941024249

(51) Int. Cl.
| | | |
|---|---|---|
| G01R 33/56 | (2006.01) | |
| G01R 33/54 | (2006.01) | |
| G06N 3/08 | (2006.01) | |
| G01R 33/34 | (2006.01) | |
| A61B 5/055 | (2006.01) | |
| G01R 33/48 | (2006.01) | |

(52) U.S. Cl.
CPC .......... *G01R 33/5608* (2013.01); *A61B 5/055* (2013.01); *G01R 33/34046* (2013.01); *G01R 33/4822* (2013.01); *G01R 33/543* (2013.01); *G06N 3/08* (2013.01)

(58) Field of Classification Search
CPC .......... G01R 33/34046; G01R 33/4822; G01R 33/543; G01R 33/5608; A61B 5/055; G01N 3/08
See application file for complete search history.

(56) References Cited

U.S. PATENT DOCUMENTS

| | | | | |
|---|---|---|---|---|
| 10,698,064 B2* | 6/2020 | Nielsen | ............. | G01R 33/4818 |
| 2009/0278539 A1* | 11/2009 | Beatty | ................ | G01R 33/5611 |
| | | | | 324/312 |
| 2013/0338484 A1* | 12/2013 | Huang | ..................... | A61N 7/02 |
| | | | | 600/411 |

(Continued)

*Primary Examiner* — Dixomara Vargas

(57) ABSTRACT

Image enhancement systems and methods with variable number of excitation (NEX) acquisitions accelerated using compressed sensing for magnetic resonance (MR) imaging are provided. The MR system comprises a body coil adapted to emit electromagnetic waves onto the anatomy of interest and receive the signals emitted from the anatomy of interest. The system comprises variable number of excitations (NEX) based compressed sensing by acquisition of different points in k-space using the body coil. A first neural network comprising an image enhancement module is provided to reconstruct the body coil images that provides a high-quality image. The high-quality image is stored in an image database. A processor is configured to connect the image database to a second neural network that is a deep learning network trained to assess the image quality and provide feedback to the processor and the first neural network.

20 Claims, 12 Drawing Sheets

(56) References Cited

U.S. PATENT DOCUMENTS

| | | | |
|---|---|---|---|
| 2018/0092569 A1* | 4/2018 | Li | G01R 33/482 |
| 2018/0292487 A1* | 10/2018 | Weingartner | G01R 33/561 |
| 2019/0147589 A1* | 5/2019 | Zhou | G06T 7/0012 |
| | | | 382/131 |
| 2019/0172230 A1* | 6/2019 | Mailhe | G06N 3/084 |
| 2019/0172570 A1* | 6/2019 | Popescu | A61N 5/1049 |
| 2019/0195975 A1* | 6/2019 | Liu | G01R 33/561 |
| 2019/0242965 A1* | 8/2019 | Nielsen | G01R 33/5608 |
| 2019/0285713 A1* | 9/2019 | Polak | G01R 33/5611 |

\* cited by examiner

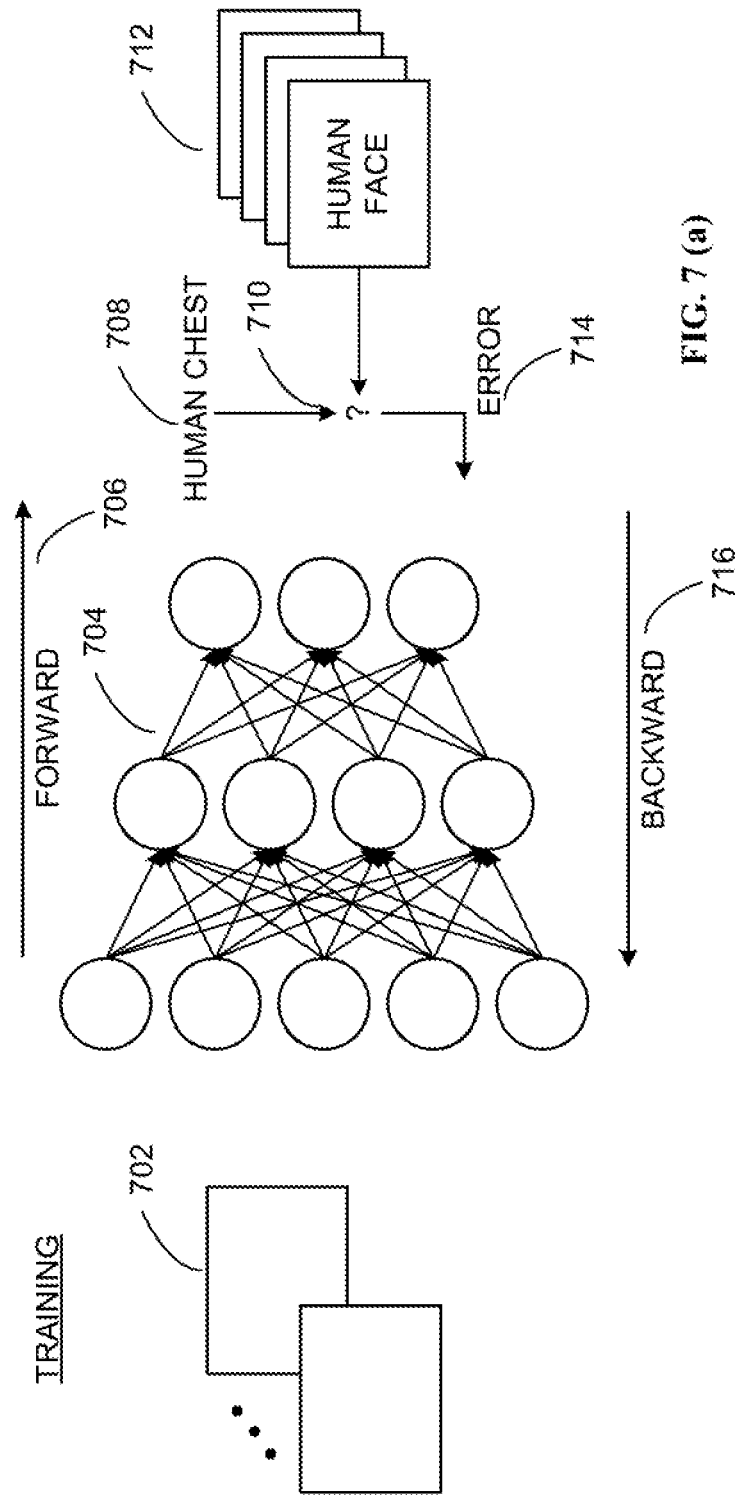

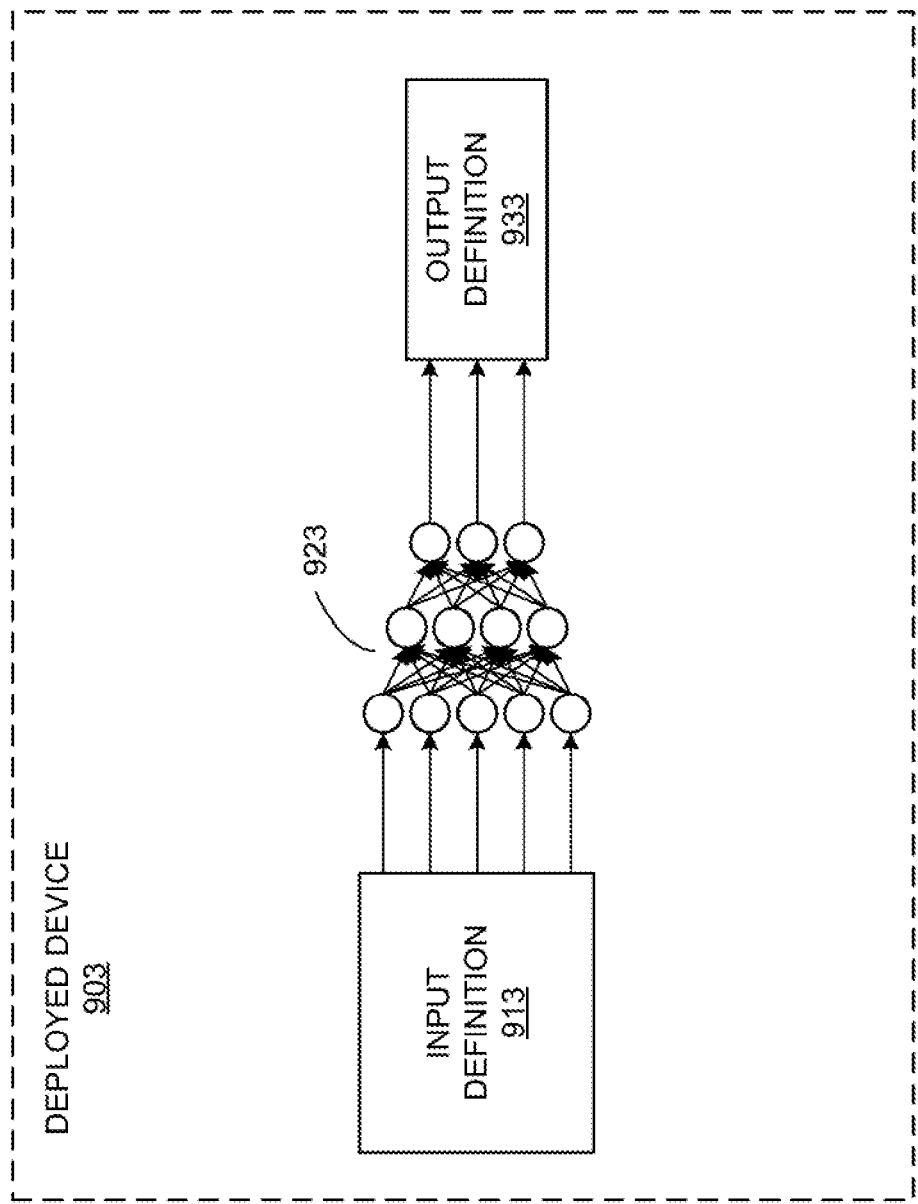

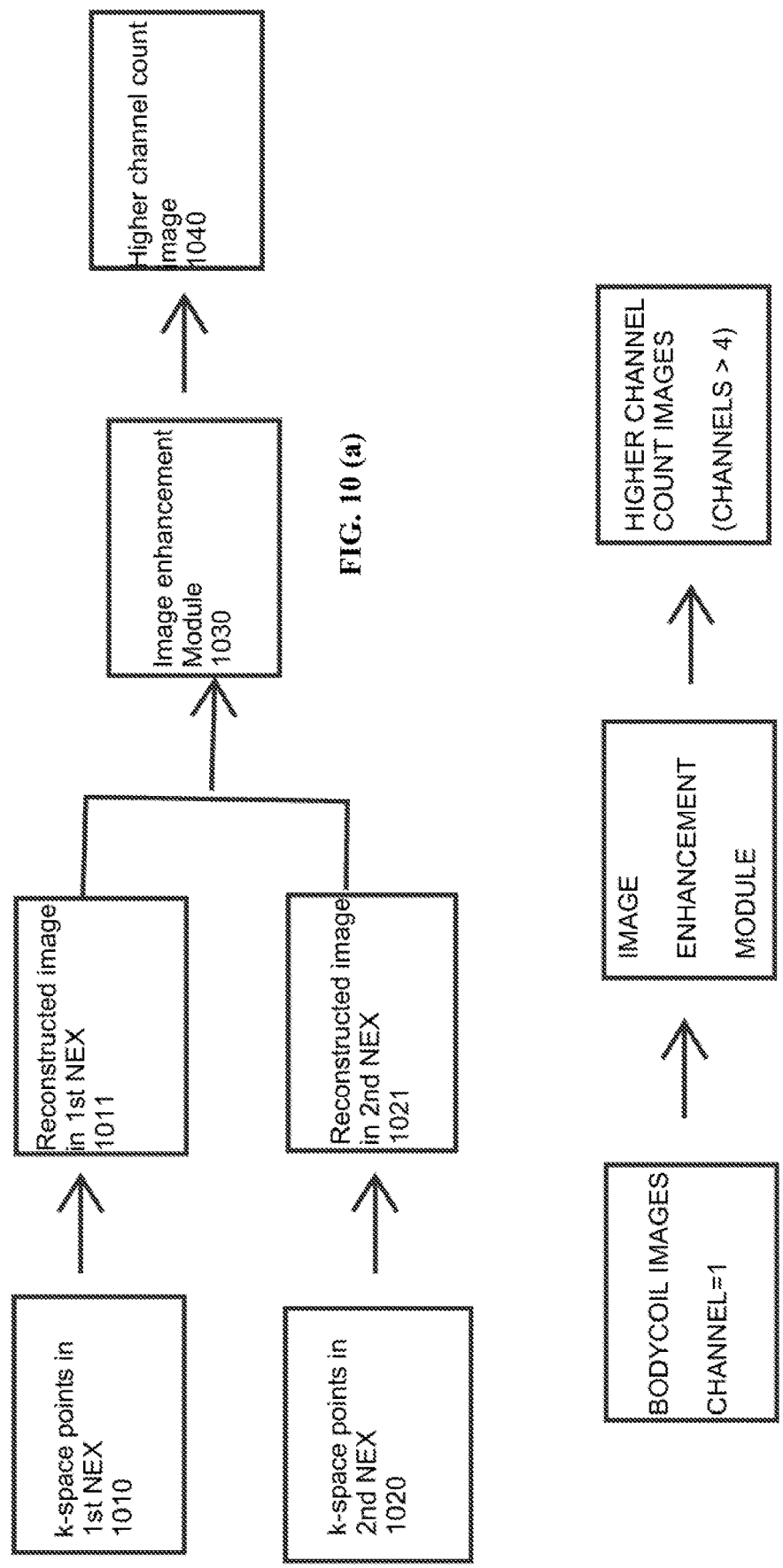

IMAGE ENHANCEMENT WITH VARIABLE NUMBER OF EXCITATION (NEX) ACQUISITIONS ACCELERATED USING COMPRESSED SENSING

CROSS-REFERENCE TO RELATED APPLICATIONS

This specification is based upon and claims the benefit of priority from Indian provisional patent application number IN 201941024249 filed on Jun. 19, 2019, and Indian non-provisional patent application number IN 201941024249 filed on Mar. 30, 2020, the entire contents of which are incorporated herein by reference.

FIELD OF THE INVENTION

Embodiments of the present specification relate generally to improved imaging systems and more particularly to volume coil signal-to-noise (SNR) ratio enhancement with variable number of excitations (NEX) acquisitions accelerated using compressed sensing in magnetic resonance (MR) imaging systems.

BACKGROUND OF THE INVENTION

Magnetic resonance (MR) imaging systems are used in the field of medical imaging to generate images of anatomical parts of the subject human body (hereinafter subject anatomy). Cost of the magnetic resonance (MR) system has direct impact on cost of the entire healthcare system. Efforts are being made worldwide to provide affordable healthcare systems and services without compromising on the output quality of devices and services.

Magnetic resonance (MR) imaging uses magnetic field gradient and radio waves to generate images of the subject anatomy. In typical magnetic resonance (MR) imaging systems, a bigger volume coil or body coil is built into the body of the magnetic resonance (MR) system for whole body scanning, however, different smaller phased array coils or surface coils may be employed for imaging specific parts of the subject anatomy. Generally, the body coil acts as a "transmitting coil" to provide a homogeneous radio frequency (RF) excitation across a large volume for whole body scans. Surface coils are positioned directly over the region of interest of the subject for receiving the signals from the subject anatomy. While fewer number of body coils are used in the magnetic resonance (MR) system, a greater number of smaller surface coils are used for conveniently placing near the subject anatomy. Surface coils have several receiving channels for receiving the signals and provide better image quality. Use of smaller surface coils closer to the subject anatomy significantly improves the image quality.

Signal-to-noise ratio (SNR) measures level of desired signal to the background noise present in the signal or ratio of the power of a signal (meaningful information) to the power of background noise (unwanted signal). A higher SNR indicates better signal quality and therefore performance of the magnetic resonance (MR) system. Increased number of receiver channels in the existing surface coils increase the SNR in current systems. The transmit and receive system is a major cost driver in current scanners. There is a great opportunity to simplify high cost receive chain and coils which will reduce cost to provide new solutions to customers in affordable markets. It is a well-known fact that the SNR drops substantially when the body coil is used as receive coil. Specifically, the SNR reduces by a factor of square root of two when compared to a fully sampled body coil acquisition (60 cm bore) to a two-fold accelerated acquisition with the eight-channel receive coil. Thus, significant cost is incurred in using separate transmission body coils and receiving surface coils. Also, there is a tradeoff between the cost of the magnetic resonance (MR) system and the image quality. While surface coils increase SNR, there is a proportionate increase in cost of the magnetic resonance (MR) system when surface coils are used.

Presently, there are no options available where cost the magnetic resonance (MR) system is reduced without compromising on image quality, SNR, scan time and system robustness.

BRIEF DESCRIPTION OF THE INVENTION

In accordance with one aspect of the invention a magnetic resonance (MR) imaging system is disclosed. The magnetic resonance (MR) imaging system comprises a body coil adapted to transmit electromagnetic waves onto the subject anatomy and acquire the signals emitted from the subject anatomy. Further, a controller is adapted to acquire electromagnetic signals from the body coil. The controller acquires distinct k-space images at a first number of excitations (NEX) and at a second number of excitations (NEX) that are different from the first number of excitations (NEX) except at the center of k-space, and the controller is configured for compressed sensing (CS) reconstruction of the k-space images. An image enhancement module receives, and processes compressed sensing (CS) reconstructed images from the controller and outputs high-quality images. The high-quality images are stored in an image database.

In accordance with another aspect of the invention a method of magnetic resonance (MR) imaging is disclosed. The method comprises transmitting electromagnetic waves using a body coil on the subject anatomy and receiving the signals from the subject anatomy. The method further comprises acquiring from the body coil distinct k-space images at a first number of excitations (NEX) and at a second number of excitations (NEX) that are different than the first number of excitations (NEX) by a controller and carrying out compressed sensing (CS) reconstruction of k-space images obtained at first number of excitations (NEX) and at a second number of excitations (NEX) to generate compressed sensing (CS) reconstructed images. Moreover, the method further comprises obtaining enhanced quality images by processing the compressed sensing (CS) reconstructed images using an image enhancement module. The method further comprises storing the high-quality images obtained from the image enhancement module and continuously assessing the quality of images using a deep learning neural network to provide feedback.

BRIEF DESCRIPTION OF THE DRAWINGS OF THE INVENTION

These and other features of the embodiments of the present specification will be better understood when the following non-limiting embodiments in the detailed description are read with reference to the accompanying drawings, wherein below:

FIG. 7 (a) illustrates example training and deployment phases of a learning neural network.

FIG. 7 (b) illustrates example training and deployment phases of a learning neural network.

FIG. 9C illustrate various deep learning device configurations.

FIG. 10 (a) illustrates an exemplary process reconstructing images based on variable NEX acquisitions accelerated using compressed sensing and image enhancement module.

FIG. 10 (b) illustrates an exemplary process reconstructing images based on variable NEX acquisitions for a single channel of the body coil.

DETAILED DESCRIPTION

The following detailed description of the exemplary embodiments refers to the accompanying drawings. The same reference numbers in different drawings identify the same or similar elements. Additionally, the drawings are not necessarily drawn to scale. Also, the following detailed description does not limit the invention. Instead, the scope of the invention is defined by the appended claims.

Reference throughout the specification to "one embodiment" or "another embodiment" or "some embodiments" means that the particular feature, structure or characteristic described in connection with an embodiment is included in at least one embodiment of the subject matter disclosed. Thus, the appearance of the phrase "in one embodiment" or "in an embodiment" or "in some embodiments" in various places throughout the specification is not necessarily referring to the same embodiment(s). Further, the particular features, structures or characteristics may be combined in any suitable manner in one or more embodiments.

Present disclosure provides a magnetic resonance (MR) imaging system that comprises a body coil adapted to transmit electromagnetic waves onto the subject anatomy and acquire the signals emitted from the subject anatomy. Further, a controller is adapted to acquire electromagnetic signals from the body coil. The controller acquires distinct k-space images at a first number of excitations (NEX) and at a second number of excitations (NEX) that are different from the first number of excitations (NEX) except at the center of k-space, and the controller is configured for compressed sensing (CS) reconstruction of the k-space images. An image enhancement module receives, and processes compressed sensing (CS) reconstructed images from the controller and outputs high-quality images. The high-quality images are stored in an image database.

Imaging devices such as magnetic resonance (MR) system generate medical images representative of the parts of the body (e.g., organs, tissues) to diagnose and/or treat diseases. Transmission, acquisition, processing, analysis, and storage of medical image data plays important roles in diagnosis and treatment of patients in healthcare.

Figure 1:
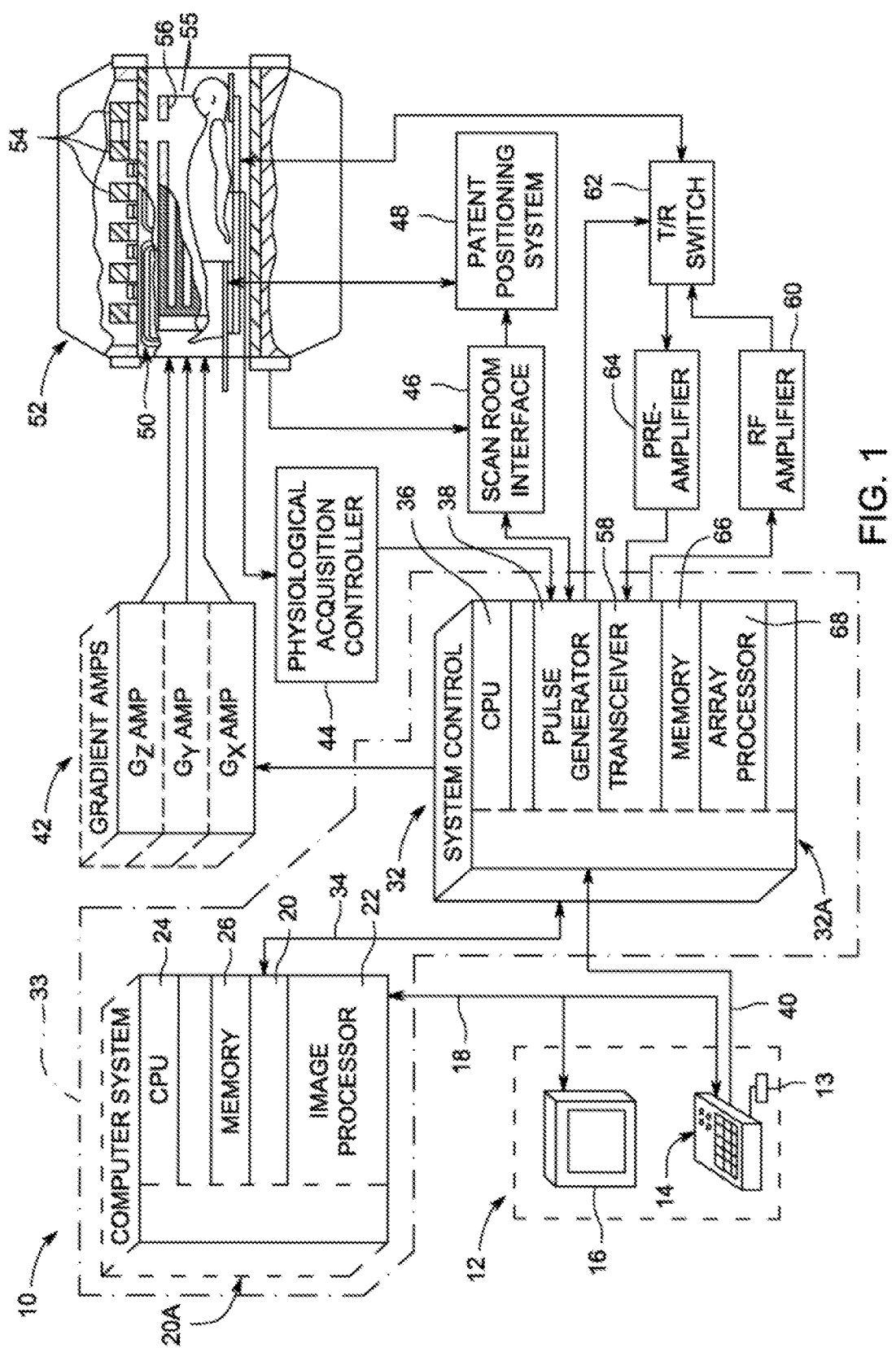
FIG. 1 illustrate an example imaging system to which the methods, apparatus, and articles of manufacture disclosed herein can be applied.

The methods, apparatus, and articles of manufacture described herein can be applied to a variety of healthcare and non-healthcare systems. In one example, the methods, apparatus, and articles of manufacture described herein can be applied to the components, configuration, and operation of a magnetic resonance (MR) imaging system. FIG. 1 illustrates an example implementation of a magnetic resonance (MR) imaging scanner apparatus to which the methods, apparatus, and articles of manufacture disclosed herein can be applied.

FIG. 1 is a schematic diagram of a magnetic resonance imaging (MRI) system 10. Operation of the system is controlled from an operator console 12, which includes an input device 13, a control panel 14, and a display screen 16. The input device 13 may be a mouse, joystick, keyboard, track ball, touch activated screen, light wand, voice control, and/or other input device. The input device 13 may be used for interactive geometry prescription. The console 12 communicates through a link 18 with a computer system 20 that enables an operator to control the production and display of images on the display screen 16. The link 18 may be a wireless or wired connection. The computer system 20 may include modules that communicate with each other through a backplane 20a. The modules of the computer system 20 may include an image processor module 22, a central processing unit (CPU) module 24, and a memory module 26 that may include a frame buffer for storing image data arrays, for example. The computer system 20 may be linked to archival media devices, permanent or back-up memory storage or a network for storage of image data and programs and communicates with a MRI system control 32 through a high-speed signal link 34. The MRI system control 32 may be separate from or integral with the computer system 20. The computer system 20 and the MRI system control 32 collectively form an "MRI controller" 33.

In the exemplary embodiment, computer system 20 includes a user interface that receives at least one input from a user. User interface may include a keyboard 806 that enables the user to input pertinent information. User interface may also include, for example, a pointing device, a mouse, a stylus, a touch sensitive panel (e.g., a touch pad and a touch screen), a gyroscope, an accelerometer, a position detector, and/or an audio input interface (e.g., including a microphone).

Moreover, in the exemplary embodiment, computer system 20 includes a presentation interface that presents information, such as input events and/or validation results, to the user. Presentation interface may also include a display adapter that is coupled to at least one display device. More specifically, in the exemplary embodiment, display device may be a visual display device, such as a cathode ray tube (CRT), a liquid crystal display (LCD), a light-emitting diode (LED) display, and/or an "electronic ink" display. Alternatively, presentation interface may include an audio output device (e.g., an audio adapter and/or a speaker) and/or a printer.

Computer system 20 also includes a processor module 22 and a memory module 26. The processor module 22 is coupled to user interface, presentation interface and memory module 26 via a system bus. In the exemplary embodiment, processor module 26 communicates with the user, such as by prompting the user via presentation interface and/or by receiving user inputs via user interface. The term "processor" refers generally to any programmable system including systems and microcontrollers, reduced instruction set computers (RISC), complex instruction set computers (CISC), application specific integrated circuits (ASIC), programmable logic circuits (PLC), and any other circuit or processor capable of executing the functions described herein. The above examples are exemplary only, and thus are not intended to limit in any way the definition and/or meaning of the term "processor."

In the exemplary embodiment, memory module 26 includes one or more devices that enable information, such as executable instructions and/or other data, to be stored and retrieved. Moreover, memory module 26 includes one or more computer readable media, such as, without limitation, dynamic random access memory (DRAM), static random access memory (SRAM), a solid state disk, and/or a hard disk. In the exemplary embodiment, memory module (26) stores, without limitation, application source code, application object code, configuration data, additional input events, application states, assertion statements, validation results, and/or any other type of data. Computer system 20, in the exemplary embodiment, may also include a communication interface that is coupled to processor module 22 via system bus. Moreover, communication interface is communicatively coupled to data acquisition devices.

In the exemplary embodiment, processor module 22 may be programmed by encoding an operation using one or more executable instructions and providing the executable instructions in memory module 26. In the exemplary embodiment, processor 814 is programmed to select a plurality of measurements that are received from data acquisition devices.

In operation, a computer system 20 executes computer-executable instructions embodied in one or more computer-executable components stored on one or more computer-readable media to implement aspects of the invention described and/or illustrated herein. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In the exemplary embodiment, the MRI system control 32 includes a modules connected together by a backplane 32*a*. These modules include a CPU module 36 as well as a pulse generator module 38. The CPU module 36 connects to the operator console 12 through a data link 40. The MRI system control 32 receives commands from the operator through the data link 40 to indicate the scan sequence that is to be performed. The CPU module 36 operates the system components to carry out the desired scan sequence and produces data which indicates the timing, strength and shape of the RF pulses produced, and the timing and length of the data acquisition window. The CPU module 36 connects to components that are operated by the MRI controller 33, including the pulse generator module 38 (which controls a gradient amplifier 42, further discussed below), a physiological acquisition controller (PAC) 44, and a scan room interface circuit 46.

In one example, the CPU module 36 receives patient data from the physiological acquisition controller 44, which receives signals from sensors connected to the patient, such as ECG signals received from electrodes attached to the patient. The CPU module 36 receives, via the scan room interface circuit 46, signals from sensors associated with the condition of the patient and the magnet system. The scan room interface circuit 46 also enables the MRI controller 33 to command a patient positioning system 48 to move the patient to a desired position for scanning.

A whole-body RF coil 56 is used for transmitting the waveform towards subject anatomy. The whole body-RF coil 56 may be a body coil (as shown in FIG. 1). An RF coil may also be a local coil 57 that may be placed in more proximity to the subject anatomy than a body coil. RF coil 57 may be a surface coil. Surface coil 57 containing receiving channels may be used for receiving the signals from the subject anatomy. Typical surface coil 57 would have eight receiving channels, however, different number of channels are possible. Using the combination of both a body coil 56 and a surface coil 57 is known to provide better image quality. Using body coil 56 as a transmit coil and a receive coil may reduce the cost of the magnetic resonance (MR) system. However, the signal-to-noise ratio (hereinafter SNR) of the MR system decreases when only body coil 56 is used The pulse generator module 38 operates the gradient amplifiers 42 to achieve desired timing and shape of the gradient pulses that are produced during the scan. The gradient waveforms produced by the pulse generator module 38 are applied to the gradient amplifier system 42 having Gx, Gy, and Gz amplifiers. Each gradient amplifier excites a corresponding physical gradient coil in a gradient coil assembly 50, to produce the magnetic field gradients used for spatially encoding acquired signals. The gradient coil assembly 50 forms part of a magnet assembly 52, which also includes a polarizing magnet 54 (which, in operation, provides a longitudinal magnetic field BO throughout a target volume 55 that is enclosed by the magnet assembly 52) and a whole-body RF coil 56 (which, in operation, provides a transverse magnetic field B1 that is generally perpendicular to B0 throughout the target volume 55). A transceiver module 58 in the MRI system control 32 produces pulses that are to be amplified by an RF amplifier 60 and coupled to the RF coil 56 by a transmit/receive switch 62. The resulting signals emitted by the excited nuclei in the subject anatomy may be sensed by the same RF coil 56 and provided to a preamplifier 64 through the transmit/receive switch 62. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 may also enable a separate RF coil (for example, a surface coil) to be used in either transmit mode or receive mode.

After the RF coil 56 picks up the MR signals produced from excitation of the target, the transceiver module 58 digitizes these signals. The MR system control 32 then processes the digitized signals by Fourier transform to produce k-space data, which then transferred the processed data to a memory module 66, or other computer readable media, via the MRI system control 32. "Computer readable media" may include, for example, structures configured so that electrical, optical, or magnetic states may be fixed in a manner perceptible and reproducible by a conventional computer (e.g., text or images printed to paper or displayed on a screen, optical discs, or other optical storage media, "flash" memory, EEPROM, SDRAM, or other electrical storage media; floppy or other magnetic discs, magnetic tape, or other magnetic storage media).

A scan is complete when an array of raw k-space data has been acquired in the computer readable media 66. This raw k-space data is rearranged into separate k-space data arrays for each image to be reconstructed, and each of these k-space data arrays is input to an array processor 68, which operates to reconstruct the data into an array of image data, using a reconstruction algorithm such as a Fourier transform. This image data is conveyed through the data link 34 to the computer system 20 and stored in memory. In response to commands received from the operator console 12, this image data may be archived in a long-term storage or may be further processed by the image processor 22 and conveyed to the operator console 12 and presented on the display 16.

In certain examples, the MRI controller 33 includes an example image processing/image quality controller implemented using at least one of the CPU 24 and/or other processor of the computer system 20A and/or the CPU 36 and/or other processor of the system control 32A and/or a separate computing device in communication with the MRI controller 33.

The current disclosure provides systems and methods of improving SNR of MR images by acquiring additional number of excitations (hereinafter NEX) using only body coil 56. The increase in NEX has a linear increase in the scan time (increasing NEX to two increases scan time by a factor of two). Parallel imaging techniques like ASSET and ARC may be used to reduce the overall scan time, even when an increased NEX is used. It is difficult, however, to implement parallel imaging with body coil 56 only. Compressed Sensing (or HyperSense) provides a viable solution to this problem.

Compressed sensing is an image processing technique for reconstructing signals and involves signal processing that allows for images to be reconstructed with MR signals having a relatively low sampling rates. MRI signals may be reconstructed to derive an image of comparable image quality if the high frequency component in k-space is sampled with less than half the sampling rate of that for low frequency and with fewer samples than that for low frequency. The lowered sampling rate increases the efficiency in storing and processing data.

Number of excitations (NEX) measures the number of times data is repeatedly acquired to form the same image. Increasing the number of excitations (NEX) will have positive impact on the SNR by factor of square root of two. Doubling the NEX will increase the SNR but also doubles the scan time.

Use of a variable NEX based compressed sensing acquisition and reconstruction with body coil 56 would have an SNR similar to images that are acquired with an eight-channel receiving coil 56 in roughly the same amount of scan time. The term variable NEX indicates acquisition of different points in k-space in each NEX. For example, if the NEX value is two, the points acquired in the first NEX is different from the points acquired in the second NEX. This enables body coil to capture distinct points in each of the acquisitions, which helps to improve the SNR when combined during reconstruction. Also, this acquisition of two different points in k-space by body coil 56 enables faster scanning and reduced scan times. The scan time reduction is accomplished by using a Compressed sensing having a greater reduction of scan time than the increase of scan time caused by multiple NEXes. For example: if acceleration factor (R=4) and NEX is two, scan time is halved. The final images may be reconstructed either using a view sharing reconstruction scheme where input points from first NEX and second NEX are combined in k-space and averaged or using a Convolutional Neural Network which has been trained to enhance appearance of a reconstructed image to look like an image obtained from an eight-channel receiving coil (RF Coil) 56 system. The body coil 56 may acquire images using the acquisition trajectories such as cartesian, spiral, radial, propeller and others well-known in the art and pulse sequence families include 2D, 3D, GRE, FSE, EPI, radial or any other mode of magnetic resonance (MR) imaging. In imaging, two timing parameters are required to be specified, repetition time (TR) and echo time (TE). Also, number of echoes in a TR called "echo train length" (ETL) may need to be specified. Longer ETLs are associated with improved signal-to-noise (SNR) ratio.

Figure 2:
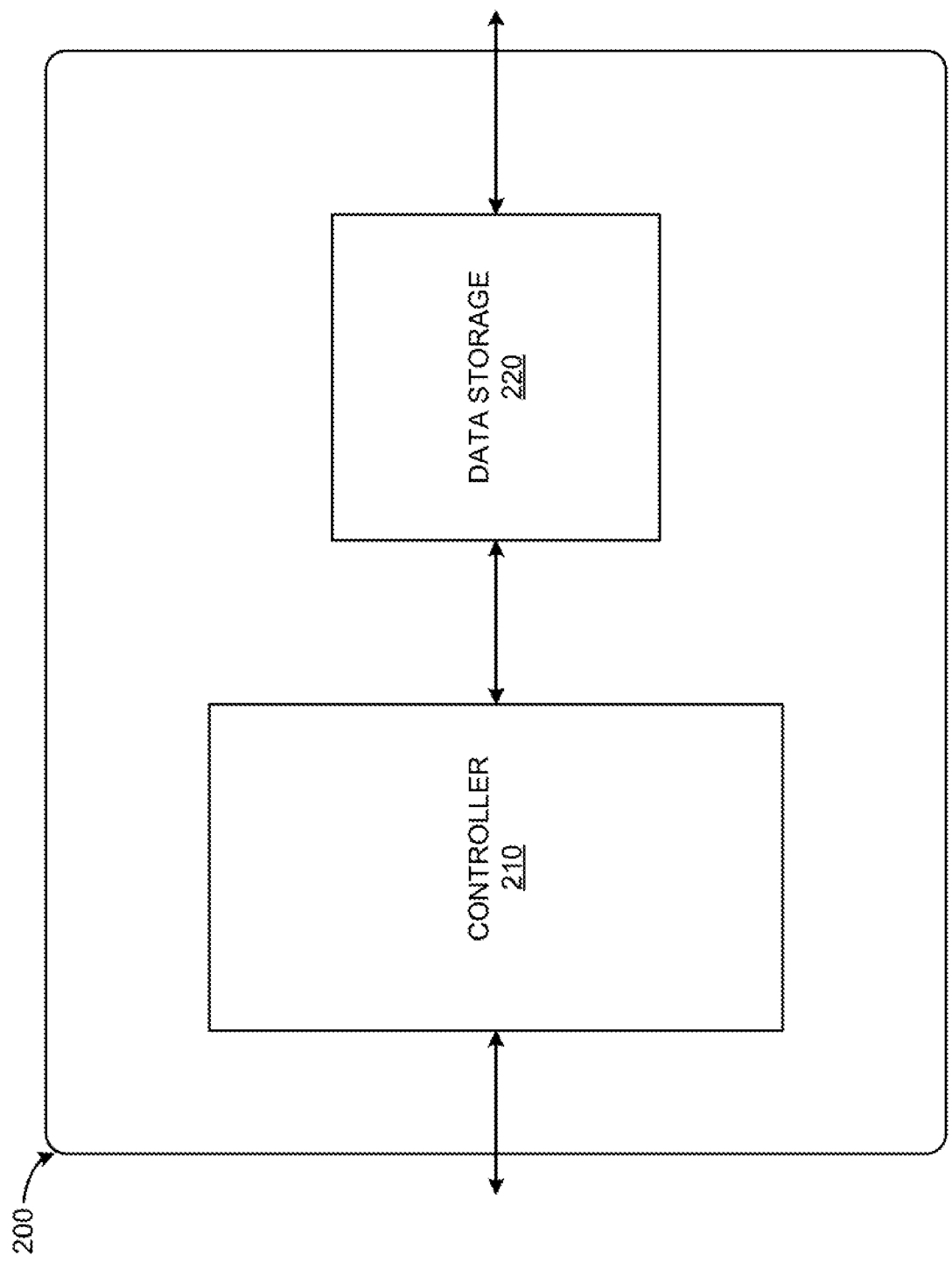
FIG. 2 illustrates an example implementation of an image quality control system.

FIG. 2 shows an example implementation of an image quality control system including a controller 210 and an associated data storage 220 (e.g., implemented in the memory 26 and/or the memory 66). In certain examples, based on prescribed, desired image processing parameters and/or image quality requirements, the controller 210 provides an intelligent model (e.g., a deep learning network model,.) to generate scan standards or reference image for a scan scenario.

In certain examples, the controller 210 includes a "smart" model that is self-tuned to learn and is updated based at least in part on an image pattern across systems in a network. In certain examples, the data storage 220 is also queried with scans obtained from different coils located over different regions and connected to a CNN network model, and preview of an image acquired with the same or similar coils in a customer network may be displayed for confirmation of the scan standards. In certain examples, the image preview is a preview of an MR image acquired previously and stored using the same network model and prescription settings closest to an output of the network model.

In certain examples, the smart model of the controller 210 includes two neural or other machine learning networks: first neural network A and second neural network B. Network A provides an improved contrast , desired SNR of anatomy obtained using body coil 56 alone or body coil 56 with the surface coil 57. At the end of a scan, a generated image is installed in the data storage 220. Network B is a trained network that compares SNR from the scanned images obtained by using only body coil 56 with the Network A images. Using this measured image quality, scan time, and SNR from the acquired image, network A is then fine-tuned by repeatedly analyzing the Network A dataset for image quality.

A medical imaging workflow and devices involved in the workflow may be configured, monitored, and updated throughout operation of the medical imaging workflow and devices using the above discussed machine learning techniques. Machine learning may be used to help configure, monitor, and update the medical imaging workflow and devices.

Machine learning techniques, whether deep learning networks or other experiential/observational learning system, may be used to locate an object in an image, understand speech and convert speech into text, and improve the relevance of search engine results, for example. Deep learning is a subset of machine learning that uses a set of algorithms to model high-level abstractions in data using a deep graph with multiple processing layers including linear and nonlinear transformations. While many machine learning systems are seeded with initial features and/or network weights to be modified through learning and updating of the machine learning network, a deep learning network trains itself to identify "good" features for analysis. Using a multilayered architecture, machines employing deep learning techniques may process raw data better than machines using conventional machine learning techniques. Examining data for groups of highly correlated values or distinctive themes is facilitated using different layers of evaluation or abstraction.

In certain examples, deep learning and/or other machine learning networks may be configured to determine an image acquisition prescription or otherwise form a data structure to instantiate image acquisition based on a desired image quality (IQ). In certain examples, multiple deep learning networks are used to generate an image quality standard.

In the exemplary embodiment, a first neural network (A) may be trained by inputting images from surface coil (RF Coil) 56 to define image quality standards. A second neural network (B) (e.g., a deep learning network, etc.) receives images acquired using the body coil 50 and learns the image quality standards periodically based on the images used for the first network.

The first neural network (A) and second neural network (B) may be provided together or separately in an image quality control framework. The first neural network (A) and/or the second neural network (B) may be deployed on a cloud, an edge device, etc., to streamline or "lighten" a host system and to aid in connecting MR scanners and/or other imaging devices in a healthcare facility (e.g., a hospital, a clinic, a surgical center, a doctor's office, etc.).

In certain examples, the image acquisition standard configuration proceeds without iteration to reduce time for setup and image acquisition. For example, the first neural network (A) is leveraged to generate standards for an image acquisition, while the second neural network (B) operates separately and simultaneously to gather and model information and periodically update and/or regenerate and redeploy the first neural network model. In addition, an expected image quality and scan time may be set before the scan is performed.

Certain examples select preferred, beneficial, or "optimal" parameters for MR imaging technologists. For example, a compromise or "trade-off" may be determined between image quality (e.g., signal-to-noise ratio (SNR) and contrast, etc.) and scan time based on the patient, study/scan type, and reason for examination. The trade-off is needed in MR imaging, for example, at least in part because prescribing a protocol having good image quality (e.g., as represented by SNR and contrast, etc.) while keeping scan time low is a complicated task for MR imaging technologists.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network may be a training network (e.g., a training network model or device) that learns patterns based on a plurality of inputs and outputs. A deep learning network may be a deployed network (e.g., a deployed network model or device) that is generated from the training network and provides an output in response to an input.

The term "supervised learning" is a deep learning training method in which the machine is provided with already-classified data from human sources. The term "unsupervised learning" is a deep learning training method in which the machine is not given already-classified data but makes the machine useful for abnormality detection. The term "semi-supervised learning" is a deep learning training method in which the machine is provided with a relatively small amount of classified data from human sources and a relatively large amount of unclassified data.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features. A CNN includes a convolutional layer where convolution is used in place of general matrix multiplication.

The term "computer aided detection" or "computer aided diagnosis" refer to detection or diagnosis using computers that analyze medical images for the purpose of suggesting a possible diagnosis.

Deep Learning and Machine Learning

Deep learning is a class of machine learning techniques employing representation learning methods that allows a machine to be given raw data and determine the representations needed for data classification. Deep learning ascertains structure in data sets using backpropagation algorithms. Deep learning machines may utilize a variety of multilayer architectures and algorithms. While machine learning, for example, involves an identification of features to be used in training the network, deep learning may process raw data to identify features of interest without the external identification.

Deep learning in a neural network environment includes numerous interconnected nodes referred to as neurons. Input neurons, activated from an outside source, activate other neurons based on connections to these other neurons which are governed by the machine operating conditions. A neural network behaves in a certain manner based on its own sequences. Learning refines the machine output, and the connections between neurons in the network such that the neural network behaves in a desired manner.

Deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data that the machine attempts to classify and ignore irrelevant background information.

Deep learning operates on the understanding that many datasets include high level features and low level features. At high level, while examining an image, for example, rather than looking for an object, it is more efficient to look for edges which form motifs which form parts, which form the object being sought. These hierarchies of features may be found in many different forms of data such as speech and text.

Learned observable features include objects and quantifiable regularities learned by the machine during supervised learning. A machine provided with a large set of well classified data is better equipped to distinguish and extract the features in successful classification of new data than the traditional algorithms that are not continuously trained to classify the data.

A deep learning machine that utilizes transfer learning may properly connect data features to certain classifications affirmed by a human expert. Conversely, the same machine may, when informed of an incorrect classification by a human expert, update the system for classification. Settings and/or other configuration information, for example, may be guided by learned use of settings and/or other configuration information, and, as a system is used more (e.g., repeatedly and/or by multiple users), a number of variations and/or other possibilities for settings and/or other configuration information may be reduced for a given situation.

An example deep learning neural network may be trained on a set of expert classified data, for example. This set of data builds the neural network, and is the stage of supervised learning. During the stage of supervised learning, the neural network may be tested whether the desired behavior has been achieved.

Once a desired neural network behavior has been achieved (e.g., a machine has been trained to operate according to a specified threshold, etc.), the machine may be deployed for use (e.g., testing the machine with "real" data, etc.). During operation, neural network classifications may be confirmed or denied (e.g., by an expert user, expert system, reference database, etc.) to continue improving neural network behavior. The example neural network is then in a state of transfer learning, as conditions for classification that determine neural network behavior are updated based on ongoing interactions. In certain examples, the neural network may provide direct feedback to other examination processes of the patient in healthcare facility that may be connected to the neural network. In certain examples, the neural network outputs data that is buffered (e.g., via the cloud, etc.) and validated before it is provided to another process.

Deep learning machines using convolutional neural networks (CNNs) may be used for image analysis. Stages of CNN analysis may be used for facial recognition in natural images, computer-aided diagnosis (CAD), etc.

Medical image data may be acquired using imaging modalities, such as magnetic resonance imaging (MRI). Medical image quality is often not affected by the machines producing the image but the patient. A patient moving during an MRI may create a blurry or distorted image that may prevent accurate diagnosis, for example.

Interpretation of medical images, regardless of quality, is only a recent development. Medical images are largely interpreted by physicians, but these interpretations may be subjective, affected by the condition of the physician's experience in the field and/or fatigue. Image analysis via machine learning may help steam-line a healthcare practitioner's workflow.

Deep learning machines may provide computer aided detection support to improve their image analysis with respect to image quality and classification, for example. However, issues faced by deep learning machines when applied to the medical field often lead to numerous false classifications. For example, deep learning machines need to overcome small training datasets and repetitive adjustments.

Deep learning machines, with minimal training, may be used to determine the quality of a medical image, for example. Semi-supervised and unsupervised deep learning machines may be used to quantitatively measure qualitative aspects of images. For example, deep learning machines may be utilized after an image has been acquired to determine if the quality of the image is sufficient for diagnosis. Supervised deep learning machines may also be used for computer aided diagnosis. Supervised learning may help reduce susceptibility to false classification, for example.

Deep learning machines may utilize transfer learning when interacting with physicians to counteract the small dataset available in the supervised training. These deep learning machines may improve computer aided diagnosis over time through training and transfer learning.

II. Description of Examples

Example Learning Network Systems

Figure 3:
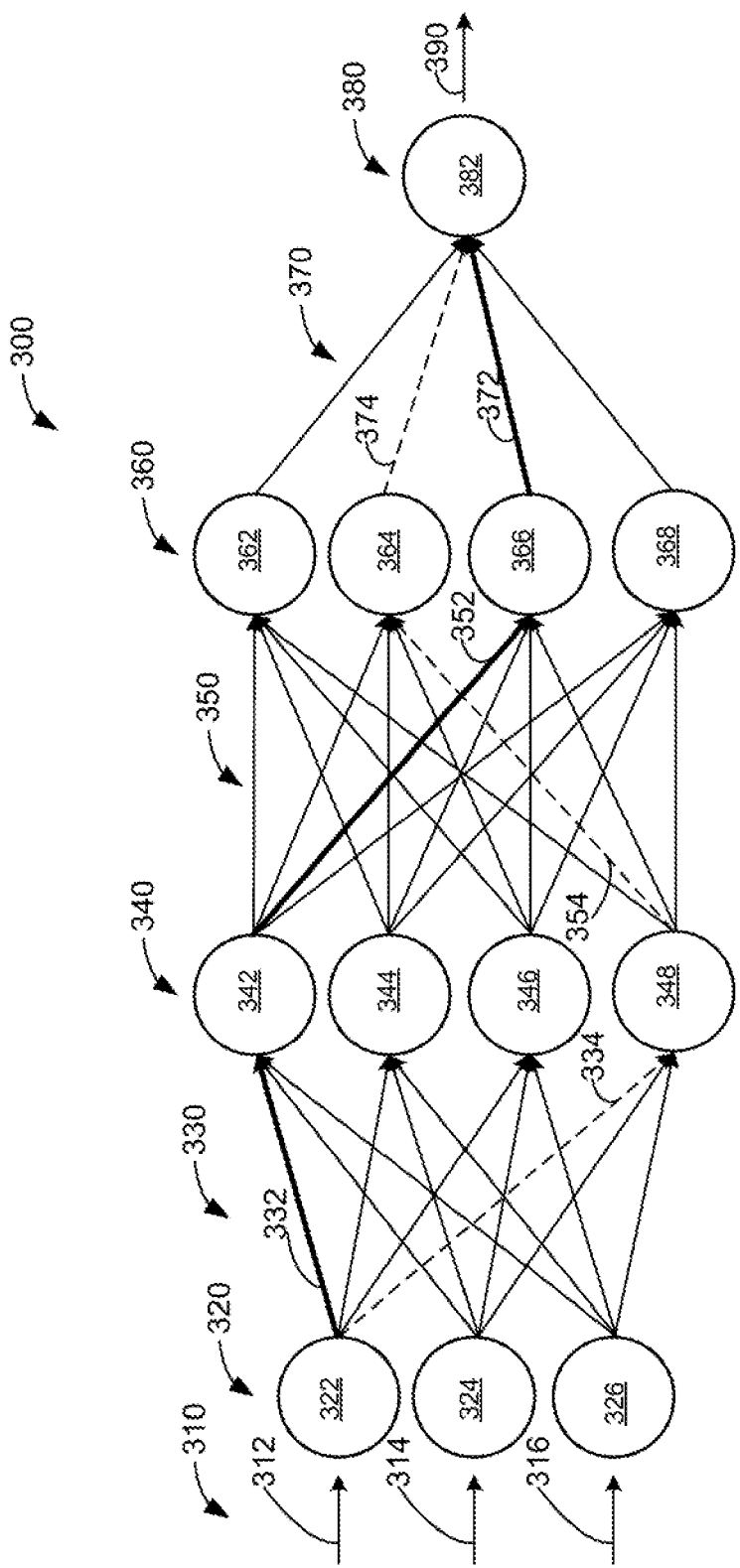
FIG. 3 is a representation of an example learning neural network.

FIG. 3 is a representation of an example learning neural network 300. The example neural network 300 includes layers 320, 340, 360, and 380. The layers 320 and 340 are connected with neural connections 330. The layers 340 and 360 are connected with neural connections 350. The layers 360 and 380 are connected with neural connections 370. Data flows forward via inputs 312, 314, 316 from the input layer 320 to the output layer 380 to provide an output 390.

The layer 320 is an input layer that, in the example of FIG. 3, includes a plurality of nodes 322, 324, 326. The layers 340 and 360 are hidden layers and include, the example of FIG. 3, nodes 342, 344, 346, 348, 362, 364, 366, 368. The neural network 300 may include more or less hidden layers 340 and 360 than shown. The layer 380 is an output layer and includes, in the example of FIG. 3, a node 382 with an output 390. Each input 312-316 corresponds to a node 322-326 of the input layer 320, and each node 322-326 of the input layer 320 has a connection 330 to each node 342-348 of the hidden layer 340. Each node 342-348 of the hidden layer 340 has a connection 350 to each node 362-368 of the hidden layer 360. Each node 362-368 of the hidden layer 360 has a connection 370 to the output layer 380. The output layer 380 has an output 390 to provide an output from the example neural network 300.

Of connections 330, 350, and 370 certain example connections 332, 352, 372 may be given added weight while other example connections 334, 354, 374 may be given less weight in the neural network 300. Input nodes 322-326 are activated through receipt of input data via inputs 312-316, for example. Nodes 342-348 and 362-368 of hidden layers 340 and 360 are activated through the forward flow of data through the network 300 via the connections 330 and 350, respectively. Node 382 of the output layer 380 is activated after data processed in hidden layers 340 and 360 is sent via connections 370. When the output node 382 of the output layer 380 is activated, the node 382 outputs an appropriate value based on processing accomplished in hidden layers 340 and 360 of the neural network 300.

Figure 4:
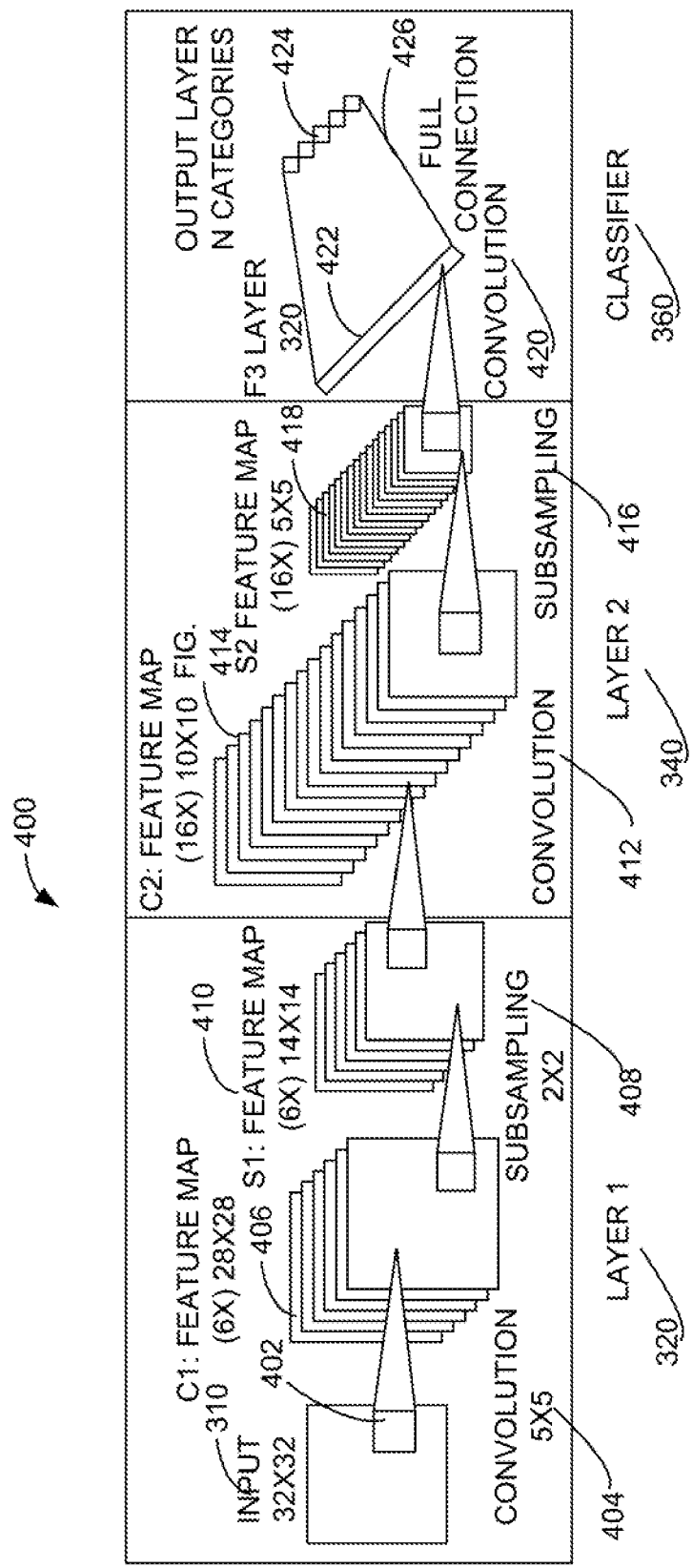
FIG. 4 illustrates an implementation of the example neural network shown in FIG. 3 as a convolutional neural network.

FIG. 4 illustrates a particular implementation of the example neural network 300 as a convolutional neural network 400. As shown in the example of FIG. 4, an input 310 is provided to the first layer 320 which processes and propagates the input 310 to the second layer 340. The input 310 is further processed in the second layer 340 and propagated to the third layer 360. The third layer 360 categorizes data to be provided to the output layer 380. More specifically, as shown in the example of FIG. 4, a convolution 404 (e.g., a 5×5 convolution, etc.) is applied to a portion or window (also referred to as a "receptive field") 402 of the input 310 (e.g., a 32×32 data input, etc.) in the first layer 320 to provide a feature map 406 (e.g., a (6×) 28×28 feature map, etc.). The convolution 404 maps the elements from the input 310 to the feature map 406. The first layer 320 also provides subsampling (e.g., 2×2 subsampling, etc.) to generate a reduced feature map 410 (e.g., a (6×) 14×14 feature map, etc.). The feature map 410 undergoes a convolution 412 and is propagated from the first layer 320 to the second layer 340, where the feature map 410 becomes an expanded feature map 414 (e.g., a (16×) 10×10 feature map, etc.). After subsampling 416 in the second layer 340, the feature map 414 becomes a reduced feature map 418 (e.g., a (16×) 4×5 feature map, etc.). The feature map 418 undergoes a convolution 420 and is propagated to the third layer 360, where the feature map 418 becomes a classification layer 422 forming an output layer of N categories 424 with connection 426 to the convoluted layer 422, for example. The output layer may provide an indication of image quality metrics based on a certain combination of image and/or imaging device input, for example.

Figure 5:
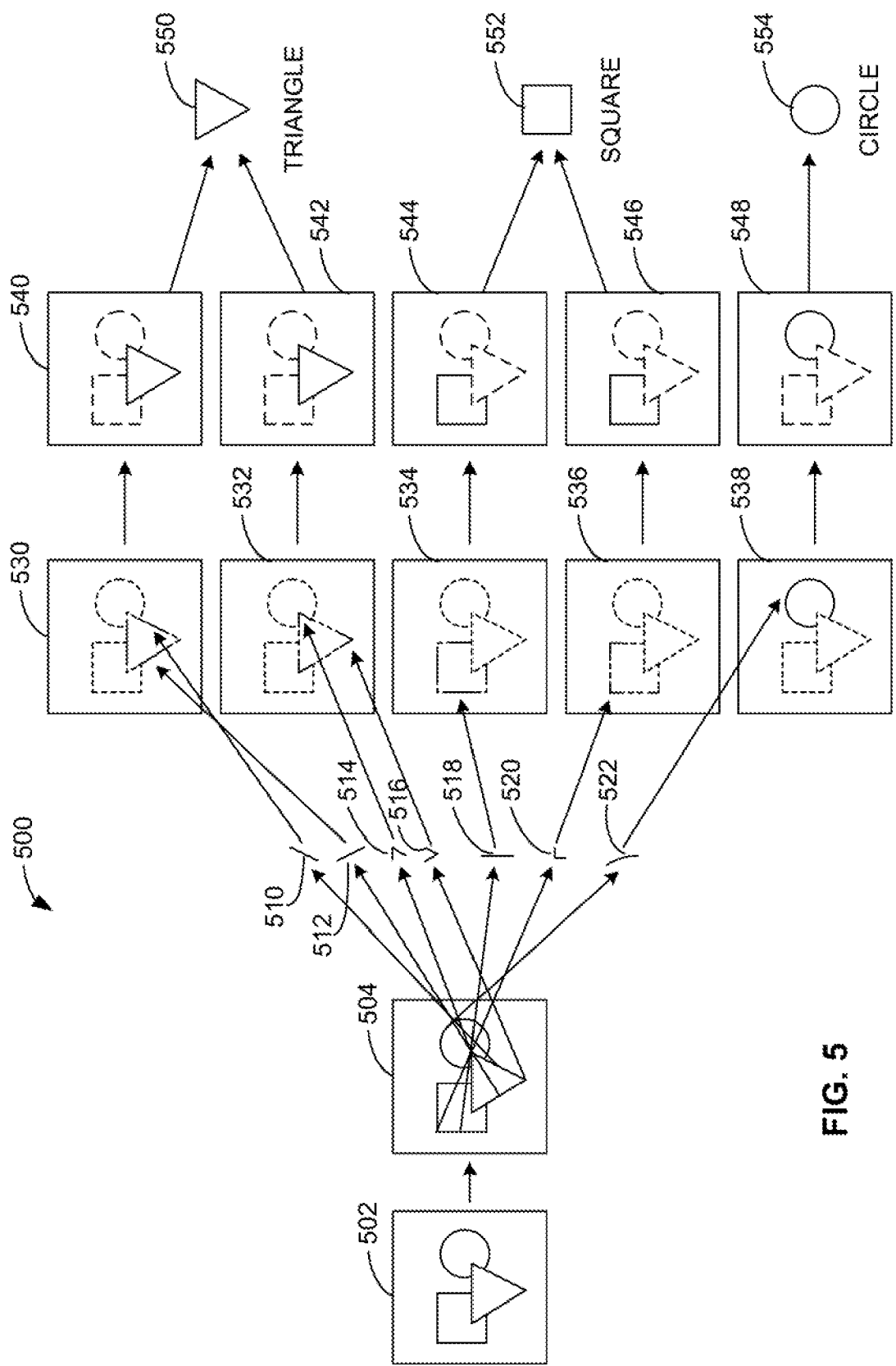
FIG. 5 is a representation of an example implementation of an image analysis convolutional neural network.

FIG. 5 is a representation of an example implementation of an image analysis convolutional neural network 500. The convolutional neural network 500 receives an input image 502 and abstracts the image in a convolution layer 504 to identify learned features 510-522. In a second convolution layer 530, the image is transformed into a plurality of images 530-538 in which the learned features 510-522 are each accentuated in a respective sub-image 530-538. The images 530-538 are further processed to focus on the features of interest 510-522 in images 540-548. The resulting images 540-548 are then processed through a pooling layer which reduces the size of the images 540-548 to isolate portions 550-554 of the images 540-548 including the features of interest 510-522. Outputs 550-554 of the convolutional neural network 500 receive values from the last non-output layer and classify the image based on the data received from the last non-output layer. In certain examples, the convolutional neural network 500 may contain many different variations of convolution layers, pooling layers, learned features, and outputs, etc.

Figure 6A:
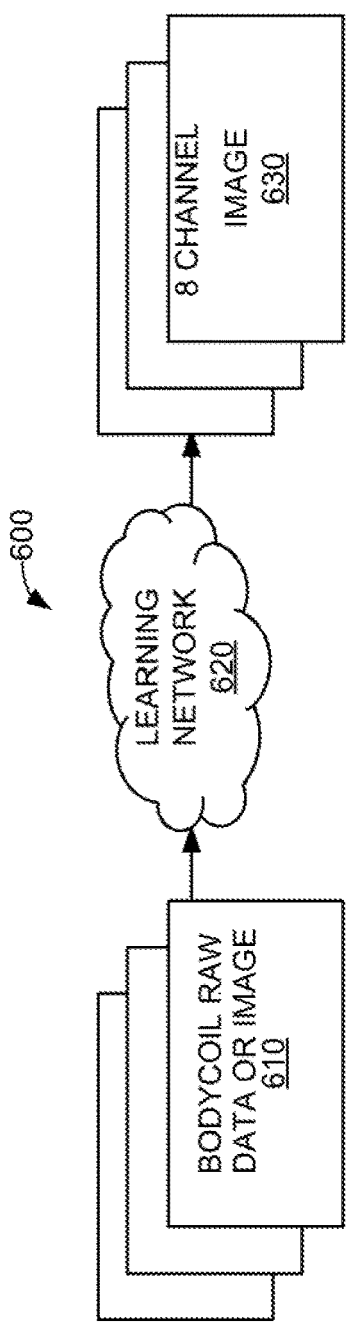
FIG. 6A illustrates an example configuration of applying a learning neural network to process and/or enhance images.

FIG. 6A illustrates an example configuration 600 for applying a learning (e.g., machine learning, deep learning, etc.) network to process and/or otherwise evaluate an image (e.g., to generate image quality information). Machine learning may be applied to a variety of processes including image acquisition, image reconstruction, image analysis/diagnosis, etc. As shown in the example configuration 600 of FIG. 6A, raw data 610 (e.g., raw data 610 such as raw image data obtained from the body coil of an MR imaging scanner) is fed into a learning network 620. The learning network 620 processes the data 610 to correlate and/or otherwise combine the raw image data 610 into a resulting image 630 (e.g., a "good quality" image and/or other image providing sufficient quality for diagnosis, etc.). The learning network 620 includes nodes and connections (e.g., pathways) to associate raw data 610 with a finished image 630. The learning network 620 may be a training network that learns the connections and processes feedback to establish connections and identify patterns, for example. The learning network 620 may be a deployed network that is generated from a training network and leverages the connections and patterns established in the training network to take the input raw data 610 and generate the resulting image 630, for example.

Once the learning network 620 is trained and produces good images 630 from the raw image data 610, the network 620 may continue the "self-learning" process and refine its performance as it operates. For example, there is "redundancy" in the input data (raw data) 610 and redundancy in the network 620, and the redundancy may be exploited.

If weights assigned to nodes in the learning network 620 are examined, there are likely many connections and nodes with very low weights. The low weights indicate that these connections and nodes contribute little to the overall performance of the learning network 620. Thus, these connections and nodes are redundant. Such redundancy may be evaluated to reduce redundancy in the inputs (raw data) 610. Reducing input 610 redundancy may result in savings in scanner hardware, reduced demands on components, and also reduced exposure dose to the patient, for example.

In deployment, the configuration 600 forms a package 600 including an input 610, a trained network 620, and an output 630. The package 600 may be deployed and installed with respect to another system, such as another MR imaging system, analysis engine, etc.

Figure 6B:
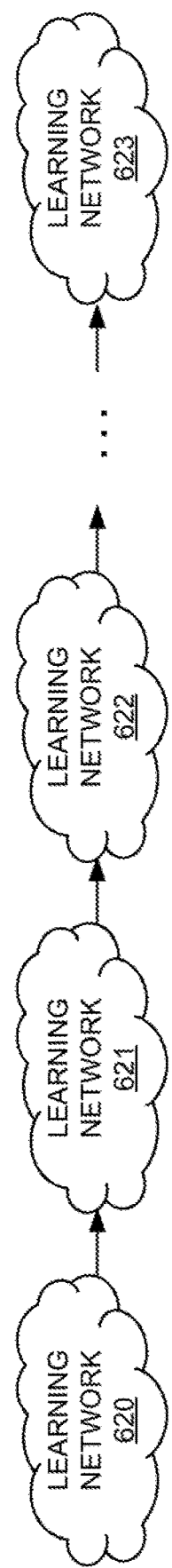
FIG. 6B illustrates a combination of a plurality of learning neural networks.

As shown in the example of FIG. 6B, the learning network 620 may be chained and/or otherwise combined with a plurality of learning networks 621-623 to form a larger learning network. The combination of networks 620-623 may be used to further refine responses to inputs and/or allocate networks 620-623 to various aspects of a system, for example.

In some examples, in operation, "weak" connections and nodes may initially be set to zero. The learning network 620 then processes its nodes in a retraining process. In certain examples, the nodes and connections that were set to zero are not allowed to change during the retraining. Given the redundancy present in the network 620, it is highly likely that equally good images will be generated. As illustrated in FIG. 6B, after retraining, the learning network 620 becomes deep learning network 621. The learning network 621 is also examined to identify weak connections and nodes and set them to zero. This further retrained network is learning network 622. The example learning network 622 includes the "zeros" in learning network 621 and the new set of nodes and connections. The learning network 622 continues to repeat the processing until a good image quality is reached at a learning network 623, which is referred to as a "minimum viable net (MVN)". The learning network 623 is a MVN because if additional connections or nodes are attempted to be set to zero in learning network 623, image quality may suffer.

Once the MVN has been obtained with the learning network 623, "zero" regions (e.g., dark irregular regions in a graph) are mapped to the input 610. The network 620-623 may or may not be simplified, but one or more of the learning networks 620-623 is processed until a "minimum viable input (MVI)" of raw data input 610 is reached. At the MVI, a further reduction in the input raw data 610 may result in reduced image 630 quality. The MVI may result in reduced complexity in data acquisition, less demand on system components, reduced stress on patients (e.g., less breath-hold or contrast), and/or reduced contrast agent doses to patients, for example.

By forcing some of the connections and nodes in the learning networks 620-623 to zero, the network 620-623 to build "collaterals" to compensate. In the process, insight into the topology of the learning network 620-623 is obtained. Note that network 621 and network 622, for example, have different topology since some nodes and/or connections have been forced to zero. This process of effectively removing connections and nodes from the network extends beyond "deep learning" and may be referred to as "deep-deep learning", for example.

FIG. 7 (a) illustrates example training and deployment phases of a learning network, such as a deep learning or other machine learning network. As shown in the example of FIG. 7 (a), in the training phase, a set of inputs 702 is provided to a network 704 for processing. In this example, the set of inputs 702 may include images obtained from the body coil 50 of an object to be identified. The network 704 processes the input 702 in a forward direction 706 to cluster data elements and identify patterns. The network 704 determines that the input 702 represents a human chest 708. In training, the network result 708 is compared 710 to a known outcome 712. In this example, the known outcome 712 is a human face (e.g., the input data set 702 represents a human face, not a human chest). Since the determination 708 of the network 704 does not match 710 the known outcome 712, an error 714 is generated. The error 714 triggers an analysis of the known outcome 712 and associated data 702 in reverse along a backward pass 716 through the network 704. Thus, the training network 704 learns from forward 706 and backward 716 passes with data 702, 712 through the network 704.

Once the network output 708 and the known output 712 match 710 according to a certain criterion or threshold (e.g., matches n times, matches greater than x percent, etc.), the training network 704 may be used to generate a network for deployment in an external system. Once deployed, a single input 720 is provided to a deployed learning network 722 to generate an output 724 as depicted in FIG. 7 (*b*). In this case, based on the training network 704, the deployed network 722 determines that the input 720 is an image of a human face 724.

Figure 8:
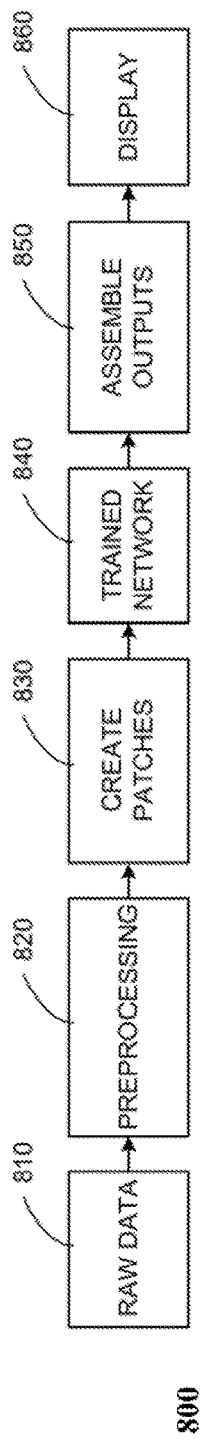
FIG. 8 illustrates a flow chart of an example method of using a trained neural network to process raw data.

FIG. 8 illustrates an example systems and methods leveraging a trained network package to provide a deep and/or other machine learning product. As shown in the example of FIG. 8, an input 810 (e.g., raw data) is provided for preprocessing 820. For example, the raw input data 810 is preprocessed 820 to check format, completeness, etc. Once the data 810 has been preprocessed 820, patches are created 830 of the data. For example, patches, portions or "chunks" of data are created 830 with a certain size and format for processing. The patches are then fed into a trained network 840 for processing. Based on learned patterns, nodes, and connections, the trained network 840 determines outputs based on the input patches. The outputs are assembled 850 (e.g., combined and/or otherwise grouped together to generate a usable output, etc.). The output is then displayed 860 and/or otherwise output to a user (e.g., a human user, a clinical system, an imaging modality, a data storage (e.g., cloud storage, local storage, edge device).

Figure 9A:
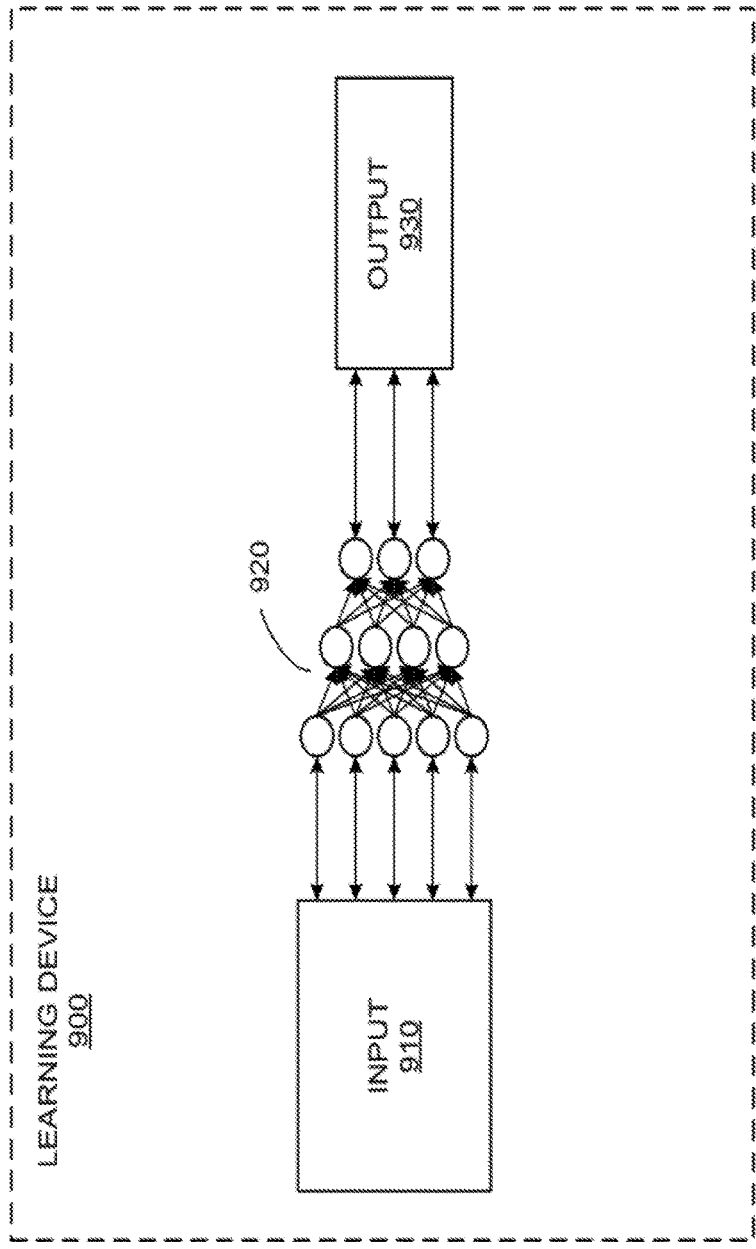
FIGS. 9A illustrates example general machine learning device.
Figure 9B:
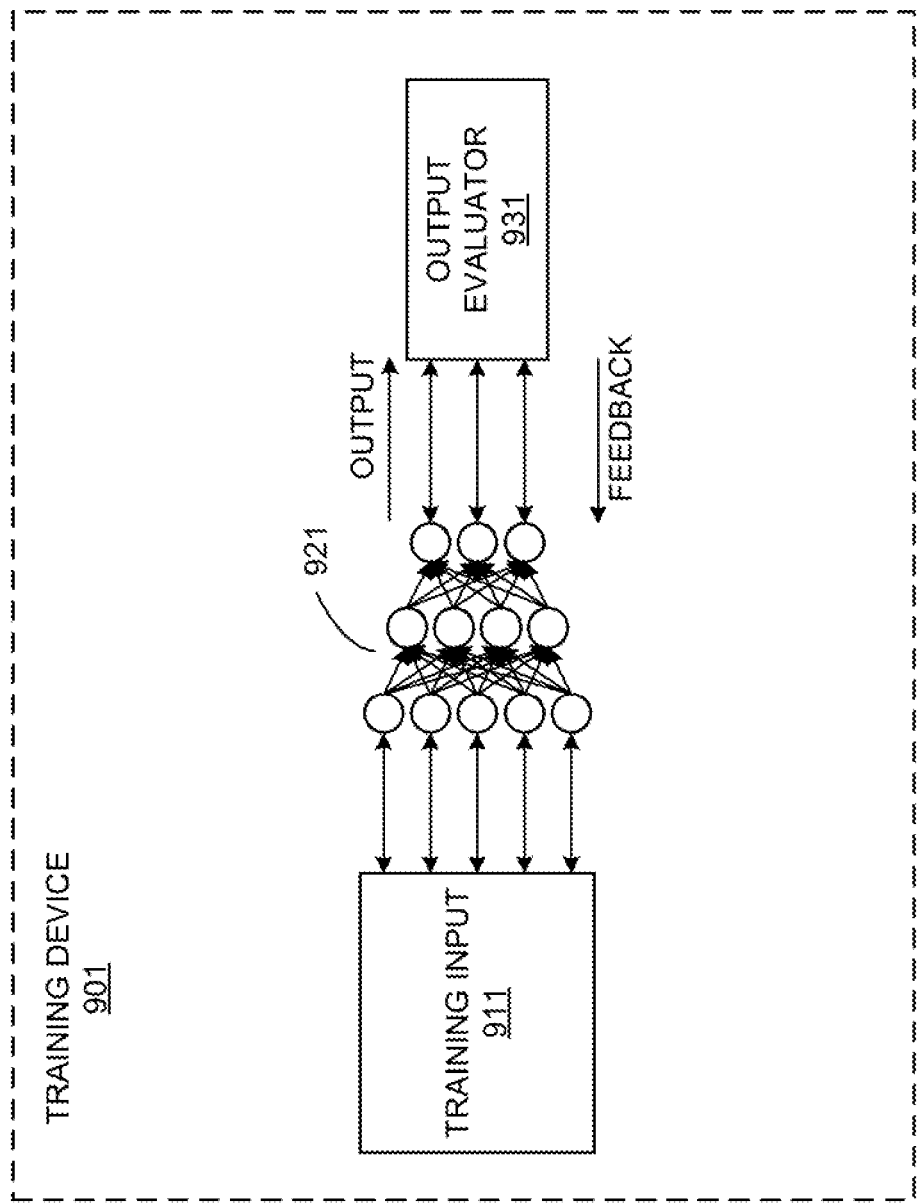
FIG. 9B illustrates an example training device

As discussed above, learning networks may be packaged as devices for training, deployment, and application to a variety of systems. FIGS. 9A-9C illustrate various learning device configurations. For example, FIG. 9A shows a general learning device 900. The example device 900 includes an input 910, a learning network model 920, and an output 930. One or more inputs 910 are translated into one or more outputs 930 via the network 920.

FIG. 9B shows an example training device 901. That is, the training device 901 is an example of the device 900 configured as a training learning network device. In the example of FIG. 9B, a plurality of training inputs 911 are provided to a network 921 to develop connections in the network 921 and provide an output to be evaluated by an output evaluator 931. Feedback is then provided by the output evaluator 931 into the network 921 to further develop (e.g., train) the network 921. Additional input 911 may be provided to the network 921 until the output evaluator 931 determines that the network 921 is trained (e.g., the output has satisfied a known correlation of input to output according to a certain threshold, margin of error, etc.).

FIG. 9C depicts an example deployed device 903. Once the training device 901 has learned to a requisite level, the training device 901 may be deployed for use. While the training device 901 processes multiple inputs to learn, the deployed device 903 processes a single input to determine an output, for example. As shown in the example of FIG. 9C, the deployed device 903 includes an input 913, a trained network 923, and an output 933. The trained network 923 may be generated from the network 921 once the network 921 has been sufficiently trained, for example. The deployed device 903 receives a system input 913 and processes the input 913 via the network 923 to generate an output 933, which may then be used by a system with which the deployed device 903 has been associated, for example.

In MR imaging, the k-space represents the spatial frequency information in two or three dimensions of an object. During MR imaging, the k-space is sampled using gradients in the phase and frequency encoding directions.

FIG. 10 illustrates an example implementation where k-space points 1010 of the subject anatomy (e.g. Human body) are acquired at first number of excitation (NEX) 1010. Subsequently, k-space points 1020 of the subject anatomy (e.g. Human body) are acquired at second number of excitation (NEX) 1020. k-space points 1020 are different from k-space points 1010. In some embodiments, k-space points 1010, 1020 may overlap at the center of k-space. Both the k-space points obtained at first NEX 1010 and second NEX 1020 are reconstructed using compressed sensing (CS) to obtain first reconstructed image 1011 and second reconstructed image 1021. Further, the first reconstructed image 1011 and second reconstructed image 1021 are sent to an image enhancement module 1030. The image enhancement module 1030 is a deep neural network architecture explained with respect to FIGS. 3-9 which is trained with input body coil 50 images against their co-registered higher channel count images as labels. The image enhancement module 1030 may either include an adder-module that averages the images 1011, 1021 or include a neural network architecture that enhances the quality of the output image 1040. Creating k-space points using a first NEX 1010 and a second NEX 1020 that is different from the first NEX 1010 using only body coil 56 allows reduction of scan time. A view sharing reconstruction scheme is thus obtained where instead of averaging multi-NEX acquisitions in image space, k-space points 1010 and 1020 are reconstructed separately to derive images 1011 and 1021 and high SNR images are derived based on images 1011 and 1021. An alternative to the above architecture could involve enhancement in k-space by converting the compressed sensing (CS) reconstructed images to k-space and either averaging or applying a Neural network in k-space to get enhanced reconstructed images. Variable NEX 2D and 3D acquisitions with Compressed Sensing acquisition and reconstruction is possible using body coil 50.

Example Image Quality Systems and Methods

Figure 11:
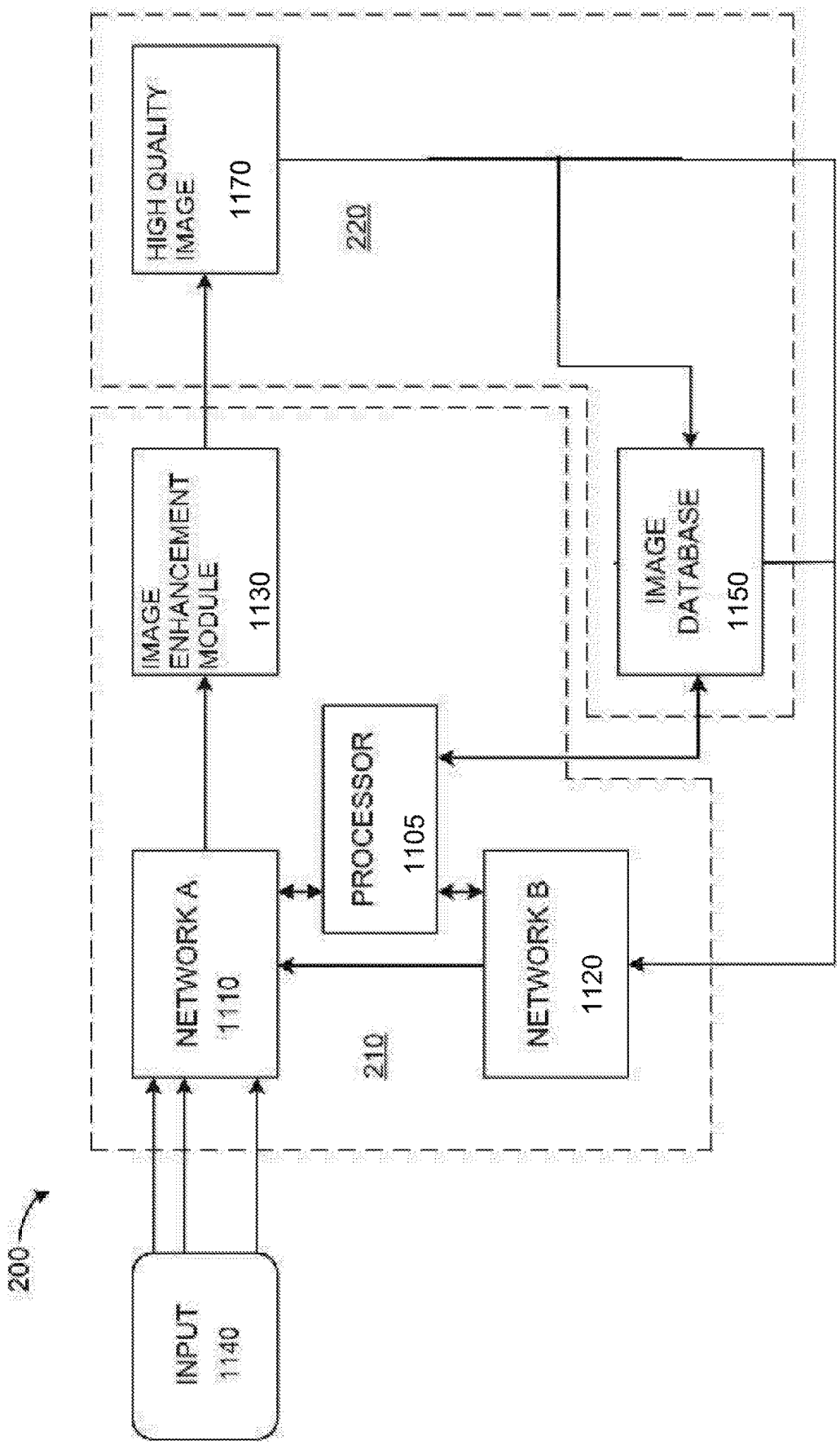
FIG. 11 illustrates a system of reconstructing images based on variable NEX acquisitions accelerated using compressed sensing with deep learning networks using the control system of FIG. 2.

FIG. 11 illustrates an example implementation of the control system 200 of FIG. 2. In the example of FIG. 11, the controller 210 includes a processor 1105, a first neural network 1110, and a second neural network 1120. The example processor 1105 is to assess the images obtained from the body coil 50 and surface coil 56. The processor 1105, controller 210, and/or all of the control system 200 may be located in the imaging device, in a workstation attached to and/or otherwise in communication with the imaging device, in a cloud-based server, in an edge device, and/or in another computing device, etc.

In certain examples, the first neural network 1110 is a trained shallow neural network with fewer layers and nodes (e.g., weighted inputs provided to a layer of radial basis functions to provide linear weights to an output,) than the neural network explained above, such as a regression neural network, etc. In certain examples, the second neural network 1120 is a more complex neural network such as a trained deep neural network (e.g., a deep convolutional neural network, other deep learning network, etc.) with a plurality of nodes and many hidden layers, etc.

For example, the shallow neural network has one hidden layer, while the deep neural network has a plurality of hidden layers. That is, the shallow network has an input layer, a hidden layer, and an output layer, and the deep network has an input layer, multiple hidden layers, and an output layer.

At first neural network 1110, body coil images are received that are transferred to image enhancement module 1130, which is a deep neural network architecture that is trained with input body coil images against their co-registered higher channel count images as labels. In one embodiment, the image enhancement module could be part of the first neural network. Output of the image enhancement module are higher quality images comparable to higher channel count images 1170. The higher quality images 1170 are stored in image database 1150 that is connected to the processor 1105. The deep learning network 1120 receives the images 1170 and leverages the image 1170 (and image(s) from the database 1150) to obtain metrics (e.g., SNR, peak SNR, contrast, mean square error, peak mean square error, mean absolute error, structural similarity index, maximum difference, absolute difference, normalized cross-correlation, structural content, image fidelity, etc.) from the image data. The metrics determined by the network 1120 may be used to periodically (e.g., after an elapsed time, after a number of executions, after feedback registers more than a threshold number of errors in actual image quality versus desired/expected/requested image quality, etc.) update the network 1110 and/or generate a new model to be deployed as the network 1110, for example.

From the foregoing, it will be appreciated that the above disclosed methods, apparatus, and articles of manufacture have been disclosed to monitor, process, and improve operation of imaging and/or other healthcare systems using a plurality of deep learning and/or other machine learning techniques.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

We claim:

1. A magnetic resonance (MR) imaging device comprising:
   a body coil adapted to transmit radio-frequency (RF) signals to a subject anatomy and acquire first MR signals from the subject anatomy in a first number of acquisition (NEX) and second MR signals from the subject anatomy in a second NEX;
   a controller adapted to control the body coil to acquire the first and second MR signals such that first k-space points corresponding to the first MR signals are distinct from second k-space points corresponding to the second MR signals in the k-space, and wherein the controller is further configured for compressed sensing (CS) reconstruction of the k-space images; and
   an image enhancement module adapted to receive the compressed sensing (CS) reconstructed images from the controller and output images of enhanced quality;
   wherein a view sharing reconstruction scheme comprises copying unacquired views in the first NEX into the second NEX and vice-versa to reconstruct images having a relatively high signal-to-noise ratio (SNR).

2. The magnetic resonance (MR) imaging device as claimed in claim 1, wherein the body coil is a single channel body coil.

3. The magnetic resonance (MR) imaging device as claimed in claim 1, wherein the controller includes a first neural network and a second neural network, wherein the first neural network is connected to the second neural network through a processor.

4. The magnetic resonance (MR) imaging device as claimed in claim 3, wherein the first neural network may be a shallow learning network, or a deep learning network and the second neural network may be a deep learning network.

5. The magnetic resonance (MR) imaging device as claimed in claim 3, the image enhancement module is located on the first neural network.

6. The magnetic resonance (MR) imaging device as claimed in claim 3, wherein the first neural network is adapted to receive MR signals acquired by the body coil and configured to generate an image having a relatively high quality based on the MR signals acquired by the body coil, wherein the first neural network is trained with the MR signals acquired by the body coil as inputs and co-registered higher channel count images as outputs.

7. The magnetic resonance (MR) imaging device as claimed in claim 3, wherein the high-quality images obtained from the image enhancement module are stored in an image database and a second neural network which is a trained deep learning network is connected to the image database through a processor to assess the quality of the images and provide feedback to the first neural network and the processor.

8. The magnetic resonance (MR) imaging device as claimed in claim 3, wherein the second neural network periodically updates the first neural network.

9. The magnetic resonance (MR) imaging device as claimed in claim 3, wherein the first neural network is fine-tuned based on quality of images associated with the imaging devices.

10. The magnetic resonance (MR) imaging device as claimed in claim 1, wherein image enhancement module comprises an adder-module that averages the images.

11. The magnetic resonance (MR) imaging device as claimed in claim 1, wherein the image enhancement module is a neural network architecture which is trained with input body coil images against their co-registered higher channel count images as labels.

12. A method of magnetic resonance (MR) imaging comprising:
   transmitting electromagnetic waves using a body coil to a subject anatomy;
   acquiring an electromagnetic signal from the subject anatomy using the body coil;
   acquiring from the body coil distinct k-space images at a first number of excitations (NEX) and at a second number of excitations (NEX) that are different than the first number of excitations (NEX) by a controller;
   carrying out compressed sensing (CS) reconstruction of k-space images obtained at first number of excitations (NEX) and at second number of excitations (NEX) to generate compressed sensing (CS) reconstructed images; and
   obtaining enhanced quality images by processing the CS reconstructed images using an image enhancement module;
   wherein the method further comprises using a reduced number of channel count as compared to any higher channel count surface coil.

13. The method of magnetic resonance (MR) imaging as claimed in claim 12, wherein obtaining enhanced quality images by processing the compressed sensing (CS) reconstructed images comprises applying a neural network to get enhanced reconstructed images.

14. The method of magnetic resonance (MR) imaging as claimed in claim 13, wherein applying the neural network to get enhanced reconstructed images comprises receiving body coil images using a first neural network having an image enhancement module to generate high quality images and storing the high-quality images in an image database.

15. The method of magnetic resonance (MR) imaging as claimed in claim 13, wherein applying a neural network to get enhanced reconstructed images comprises training a second neural network with body coil images, and assessing the high-quality images stored in the image database to the images stored on the trained second neural network and providing feedback to the first neural network.

16. The method of magnetic resonance (MR) imaging as claimed in claim 13, further comprising fine tuning the first neural network based on the quality of images associated with the imaging device.

17. The method of magnetic resonance (MR) imaging as claimed in claim 12, wherein any parameter combination of repetition time (TR), echo time (TE), and echo tail length (ETL) is used in generating a variation in contrast.

18. The method of magnetic resonance (MR) imaging as claimed in claim 12, wherein compressed sensing (CS) reconstruction of k-space images includes variable acceleration factors for each number of excitations (NEX).

19. A magnetic resonance (MR) imaging device comprising:
  a body coil adapted to transmit radio-frequency (RF) signals to a subject anatomy and acquire first MR signals from the subject anatomy in a first number of acquisition (NEX) and second MR signals from the subject anatomy in a second NEX;
  a controller adapted to control the body coil to acquire the first and second MR signals such that first k-space points corresponding to the first MR signals are distinct from second k-space points corresponding to the second MR signals in the k-space, and wherein the controller is further configured for compressed sensing (CS) reconstruction of the k-space images;
  an image enhancement module adapted to receive the compressed sensing (CS) reconstructed images from the controller and output images of enhanced quality;
  wherein the controller includes a first neural network and a second neural network, wherein the first neural network is connected to the second neural network through a processor; and
  wherein the first neural network is adapted to receive MR signals acquired by the body coil and configured to generate an image having a relatively high quality based on the MR signals acquired by the body coil, wherein the first neural network is trained with the MR signals acquired by the body coil as inputs and co-registered higher channel count images as outputs.

20. A magnetic resonance (MR) imaging device comprising:
  a body coil adapted to transmit radio-frequency (RF) signals to a subject anatomy and acquire first MR signals from the subject anatomy in a first number of acquisition (NEX) and second MR signals from the subject anatomy in a second NEX;
  a controller adapted to control the body coil to acquire the first and second MR signals such that first k-space points corresponding to the first MR signals are distinct from second k-space points corresponding to the second MR signals in the k-space, and wherein the controller is further configured for compressed sensing (CS) reconstruction of the k-space images;
  an image enhancement module adapted to receive the compressed sensing (CS) reconstructed images from the controller and output images of enhanced quality; and
  wherein the image enhancement module is a neural network architecture which is trained with input body coil images against their co-registered higher channel count images as labels.

* * * * *